(12) United States Patent
Springer, Jr.

(10) Patent No.: US 8,043,349 B2
(45) Date of Patent: Oct. 25, 2011

(54) CONFIGURABLE PHOTOTHERAPY DEVICE

(75) Inventor: Jack F. Springer, Jr., Fort Edward, NY (US)

(73) Assignee: Medtek Lighting Corporation, Hudson Falls, NY (US)

( * ) Notice: Subject to any disclaimer, the term of this patent is extended or adjusted under 35 U.S.C. 154(b) by 0 days.

(21) Appl. No.: 12/025,655

(22) Filed: Feb. 4, 2008

(65) Prior Publication Data

US 2009/0012588 A1    Jan. 8, 2009

Related U.S. Application Data

(60) Provisional application No. 60/887,838, filed on Feb. 2, 2007.

(51) Int. Cl.
*A61N 5/06* (2006.01)

(52) U.S. Cl. .................. 607/94; 607/88; 607/89

(58) Field of Classification Search .............. 607/94, 607/88; 606/9; 108/8, 57.2, 57.21, 55.3, 108/50.02, 99; 248/297.1, 297.3, 274.1, 248/188.7; 361/681

See application file for complete search history.

(56) References Cited

U.S. PATENT DOCUMENTS

| | | | |
|---|---|---|---|
| 4,740,707 A * | 4/1988 | Thaw | 607/94 |
| 4,866,284 A * | 9/1989 | Frankena et al. | 250/494.1 |
| 5,957,959 A * | 9/1999 | Rissmaney et al. | 607/88 |
| 6,402,774 B1 * | 6/2002 | Caldironi | 607/91 |
| 2002/0011544 A1* | 1/2002 | Bosson | 248/121 |
| 2003/0004499 A1* | 1/2003 | McDaniel | 606/3 |
| 2004/0035987 A1* | 2/2004 | Oddsen, Jr. | 248/121 |
| 2004/0251388 A1* | 12/2004 | Williams | 248/274.1 |
| 2005/0085875 A1* | 4/2005 | Van Zuylen | 607/88 |
| 2005/0234327 A1* | 10/2005 | Saracen et al. | 600/407 |
| 2006/0054751 A1* | 3/2006 | Johnson et al. | 248/123.11 |
| 2006/0229689 A1* | 10/2006 | Ferguson et al. | 607/88 |
| 2007/0191822 A1* | 8/2007 | McDaniel | 606/9 |
| 2007/0252919 A1* | 11/2007 | McGreevy | 348/825 |
| 2008/0125834 A1* | 5/2008 | Hendrix et al. | 607/88 |

* cited by examiner

*Primary Examiner* — Ahmed M Farah
*Assistant Examiner* — Jeffrey Lipitz
(74) *Attorney, Agent, or Firm* — Baker Botts LLP

(57) ABSTRACT

Disclosed herein is a device which includes a first panel, a second panel, a center panel, an upright support (pillar), and a base. The first and second panels each include one or more ultraviolet lamps. The center panel may optionally include one or more ultraviolet lamps. The panels are mounted to a swivel plate, which is in turn mounted to the upright support. The swivel plate allows the panels to be rotated by approximately 90 degrees. The upright support has a track that allows the swivel plate to move up and down the upright support.

6 Claims, 9 Drawing Sheets

CONFIGURABLE PHOTOTHERAPY DEVICE

CROSS-REFERENCE TO RELATED APPLICATIONS

This application is claims priority to U.S. Provisional Application Ser. No. 60/887,838, filed Feb. 2, 2007, which is hereby incorporated by reference in its entirety herein.

TECHNICAL FIELD

The present invention relates generally to phototherapy systems and more specifically to a configurable phototherapy system used to treat various body parts.

BACKGROUND

Contemporary phototherapy systems used in the treatment of psoriasis and other skin diseases are typically designed to treat only one or two areas of the body. One device currently on the market features a single body-sized panel that is used for treating the front or back of the patient. Another device used for treating the face and chest area features a smaller table-top panel. If the patient requires ultraviolet treatment on his or her hands or feet, yet another system is required. In addition, scalp treatment may involve the use of an ultraviolet comb or wand.

For patients with skin diseases on multiple areas of the body, treatment may involve the use of several different phototherapy systems. If the patient desires or requires treatment at home, the cost of purchasing multiple phototherapy systems and/or the space required to store them may prove prohibitive.

There therefore exists a need for a device that reduces the number of phototherapy systems required to treat multiple areas of the body.

SUMMARY

The present invention provides a device suited to treating psoriasis and other skin diseases on multiple parts of the body. The device may be used to treat various body parts, including the hands, feet, face, chest, scalp, and the back and front of the torso.

The device includes a first panel, a second panel, a center panel, an upright support (pillar), and a base. The first and second panels each include one or more ultraviolet lamps. The center panel may optionally include one or more ultraviolet lamps. The panels are mounted to a swivel plate, which is in turn mounted to the upright support.

The swivel plate allows the panels to be rotated by approximately 90 degrees. The upright support has a track that allows the swivel plate to move up and down the upright support.

A pulley system may be utilized to enable the panels to be moved vertically up or down. A spring with a knob may also be utilized to stop the panels at a desired height. In one arrangement, the pulley system includes a cable connected to the center panel and a pulley which is connected to the upright support. A cam allows the panels to fold forward to face each other or to be pushed flat to lie in the same plane. A spring pin with a knob locks the panels into the desired cam position.

Alternatively, a crank system may be used to move the panels up and down. Each panel can be connected to an on/off switch so that it can be powered off when not needed for treatment.

The device can be configured to treat more than one body part. To treat the upper or lower body, for example, the panels can be rotated into the starting position, raised or lowered to the appropriate height, and either folded forward to surround the body or unfolded to lie in a plane parallel to the body. To treat the hands, for example, the panels can be folded forward to face each other, rotated by 90 degrees so as to be parallel to the floor, and lowered to the appropriate height.

BRIEF DESCRIPTION OF THE DRAWINGS

Further features and advantages of the disclosed subject matter will become apparent from the following detailed description taken in conjunction with the accompanying figures showing illustrative embodiments of the disclosed subject matter, in which.

DETAILED DESCRIPTION

Figure 1:
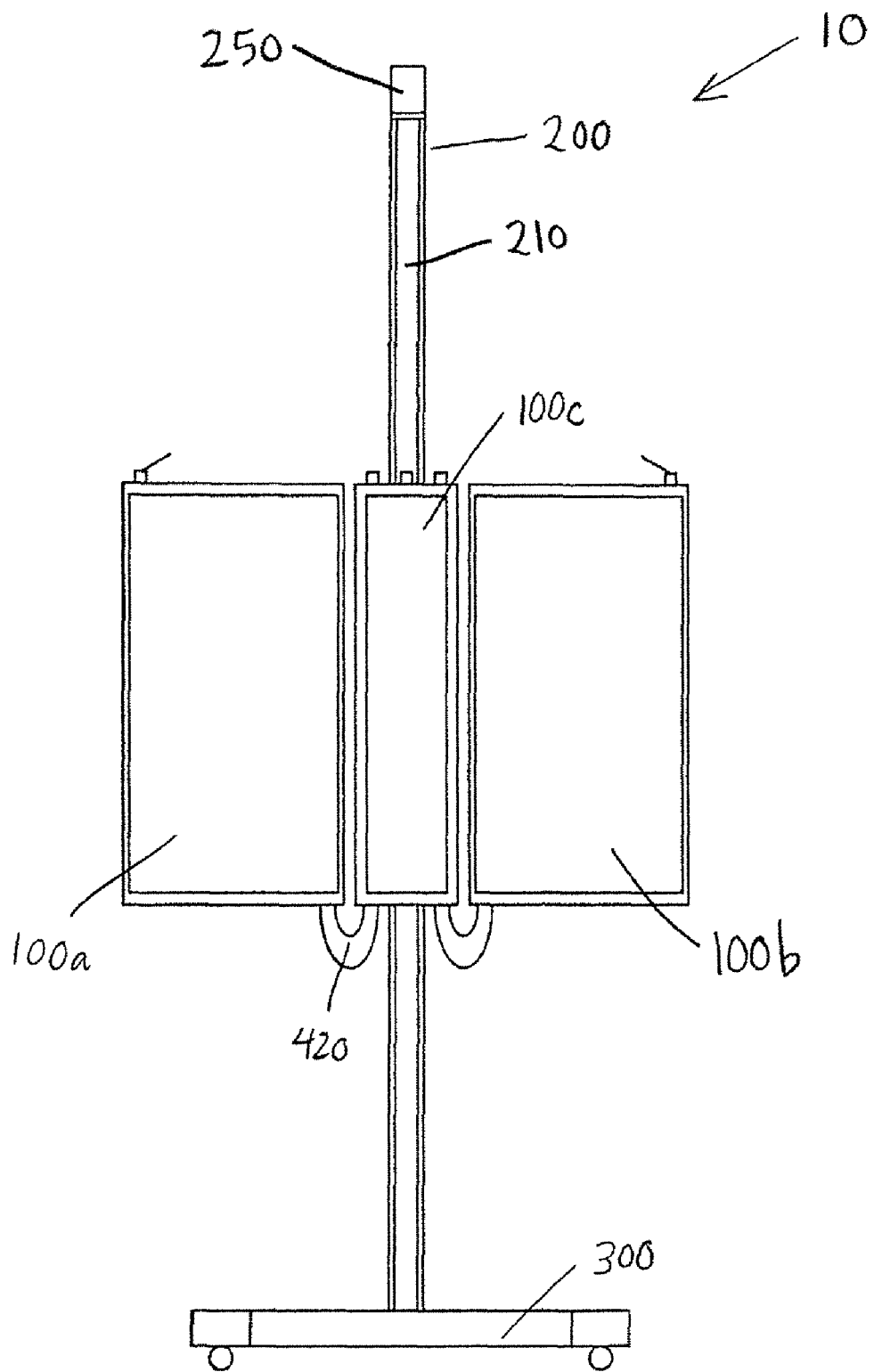
FIG. 1 is a front view of one embodiment of the disclosed subject matter.
Figure 2:
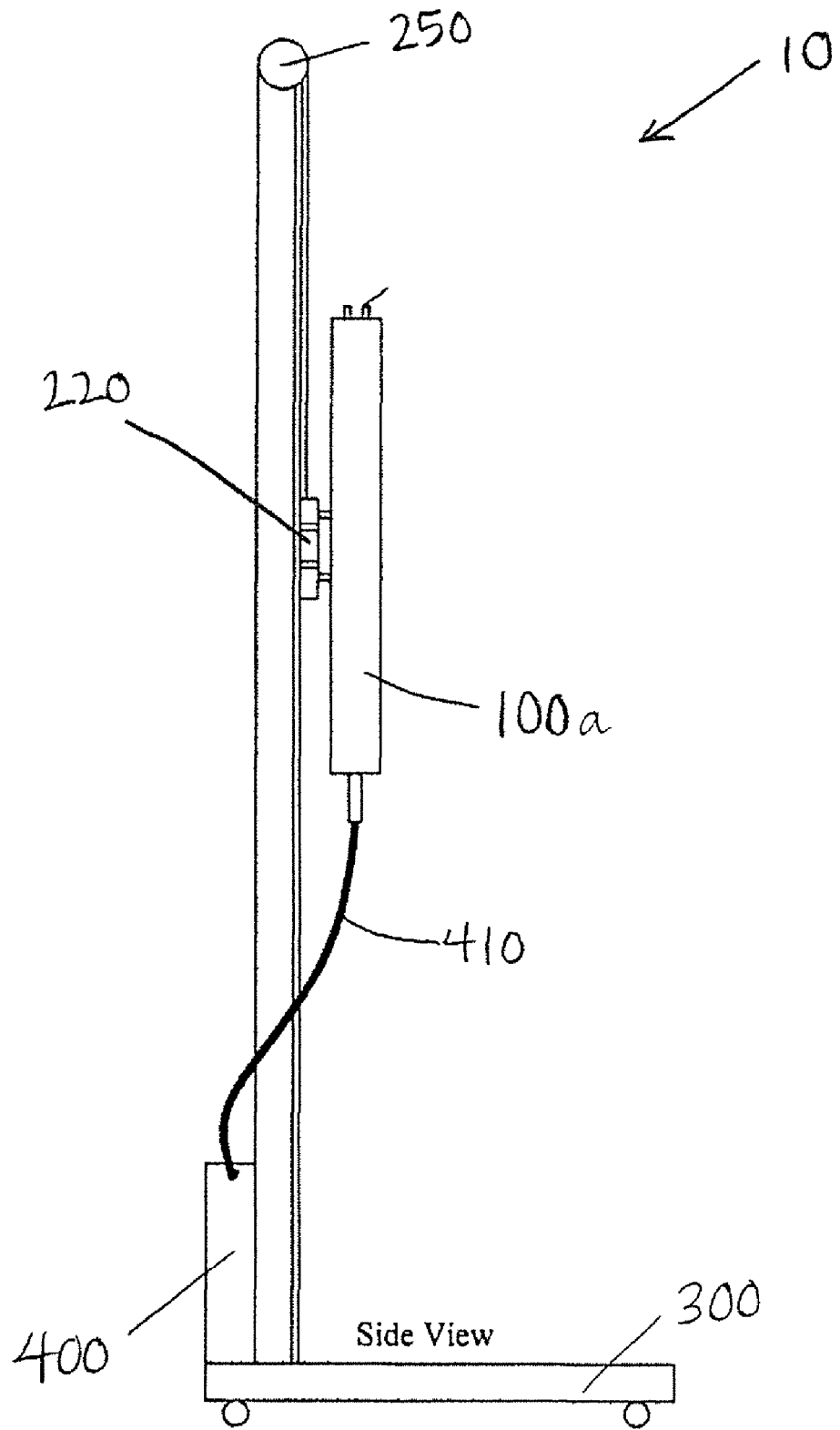
FIG. 2 is an side view of the embodiment depicted in FIG. 1.
Figure 3:
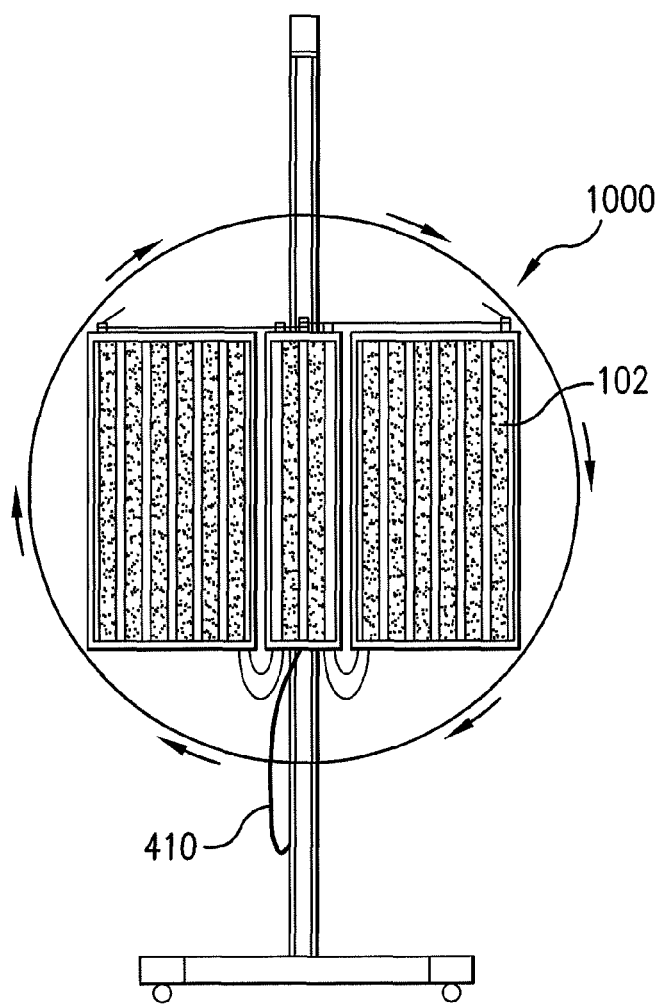
FIG. 3 is a front view of one embodiment of the disclosed subject matter illustrating how the panels may be rotated.
Figure 4:
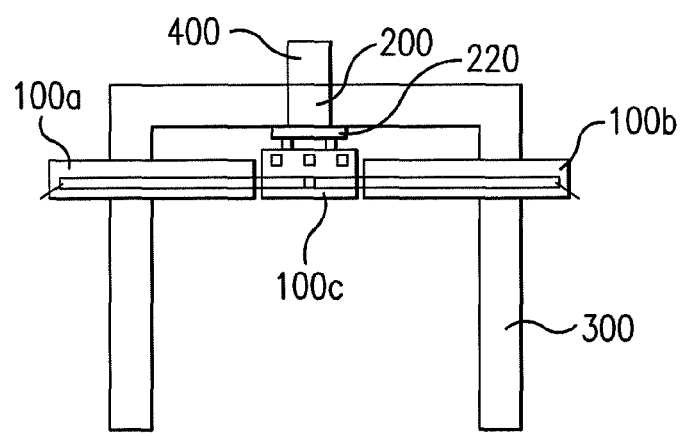
FIG. 4 is a top view of the embodiment depicted in FIG. 3.

In one embodiment, as shown in FIGS. 1-4, the configurable phototherapy device 10 includes a first panel 100a, a second panel 100b, a center panel 100c, an upright support (pillar) 200, and a base 300. Preferably, the upright support 200 is approximately 82⅛ inches high, but the height may range from 36 inches to 100 inches. Preferably, the base is 28 inches wide and 27 inches deep, but the width may range from 6 inches to 60 inches, and the depth may range from 12 inches to 60 inches. The panels 100a and 100b include one or more ultraviolet lamps 102. Preferably, the first panel 100a and second panel 100b are each approximately 27⅜ inches high and 14 inches wide, but the height may range from 10 inches to 48 inches and the width may range from 4 inches to 36 inches. The center panel 100c can include one or more ultraviolet lamps 102 or can be implemented without lamps. Preferably, the center panel is approximately 6⅝ inches wide, but the width may range from 2 inches to 36 inches.

Figure 5:
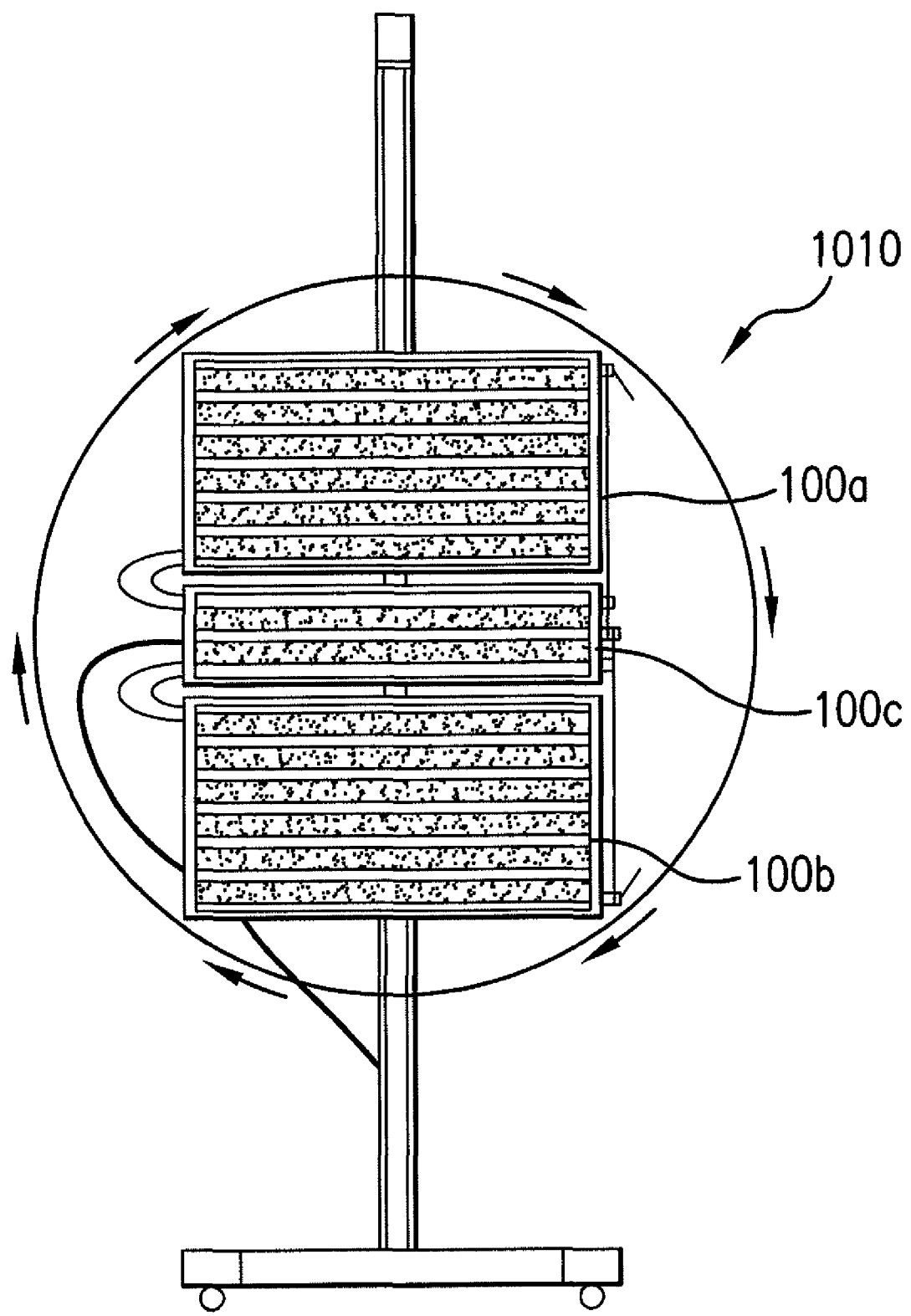
FIG. 5 is an front view of one embodiment of the disclosed subject matter illustrating the 90-degree rotation position.

The panels 100 are mounted to a swivel plate 220, which allows them to be rotated from the starting position 1000 to the 90-degree rotation position 1010 shown in FIG. 5.

The upright support 200 includes a track 210 that allows the swivel plate 220 to move up and down the upright support 200. A pulley system 250 can be used to allow the panels 100 to be moved vertically up or down. Preferably, the cable in the pulley system is connected to the swivel plate 220. Preferably, the cable is made of rope or metallic chain, but other materials may be used. A spring with a knob may also be utilized to stop the panels 100 at a desired height.

Alternatively, a gear system may be used to move the panels up and down. The gear system can be hand-cranked or motor-driven.

A cam allows the panels 100a and 100b to fold forward to face each other or to be pushed flat to lie in the same plane. A spring pin with a knob locks the panels 100a and 100b into the desired cam position. Each panel may be connected to an on/off switch so that it can be powered off when not needed for treatment. In addition, the base 300 can be mounted on casters 320 to allow the device to be moved around.

Preferably, the upright support 200 and base 300 are made of steel, but aluminum, fiberglass, plastic, and other materials may also be used.

Figure 6:
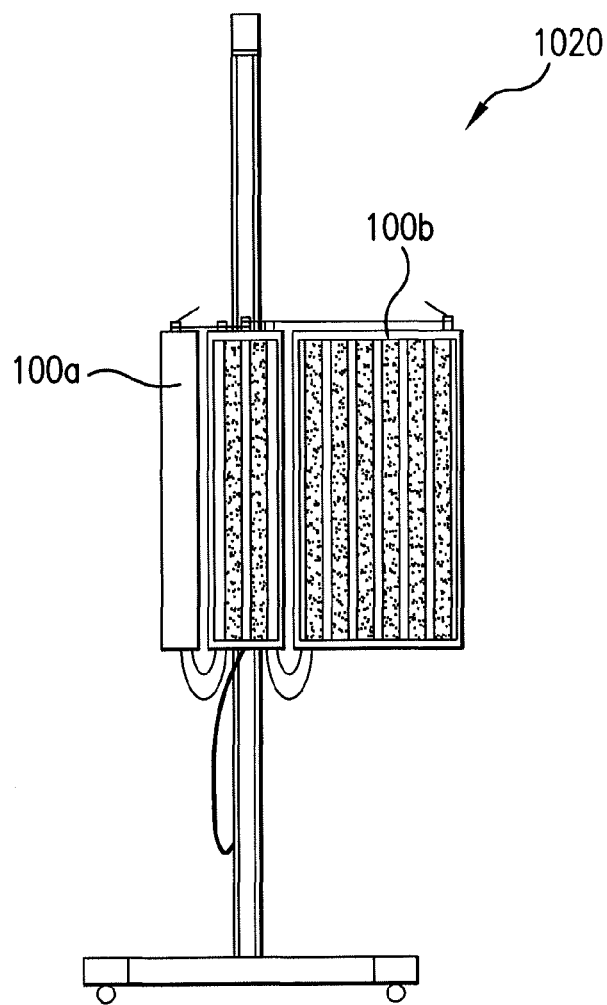
FIG. 6 is a front view of one embodiment of the disclosed subject matter in the left-forward position.
Figure 7:
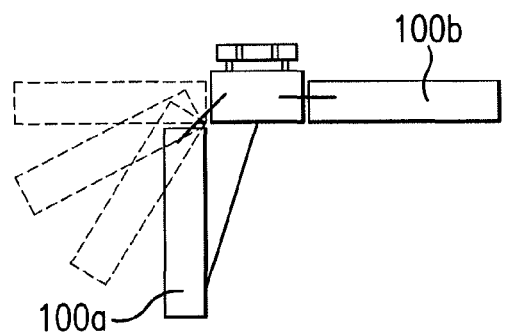
FIG. 7 is a top view of the embodiment depicted in FIG. 6.

FIGS. 6 and 7 illustrate the device configured in the left-forward position 1020. The first panel 100a has been pulled forward while the second panel 100b remains in a flat position.

Figure 8:
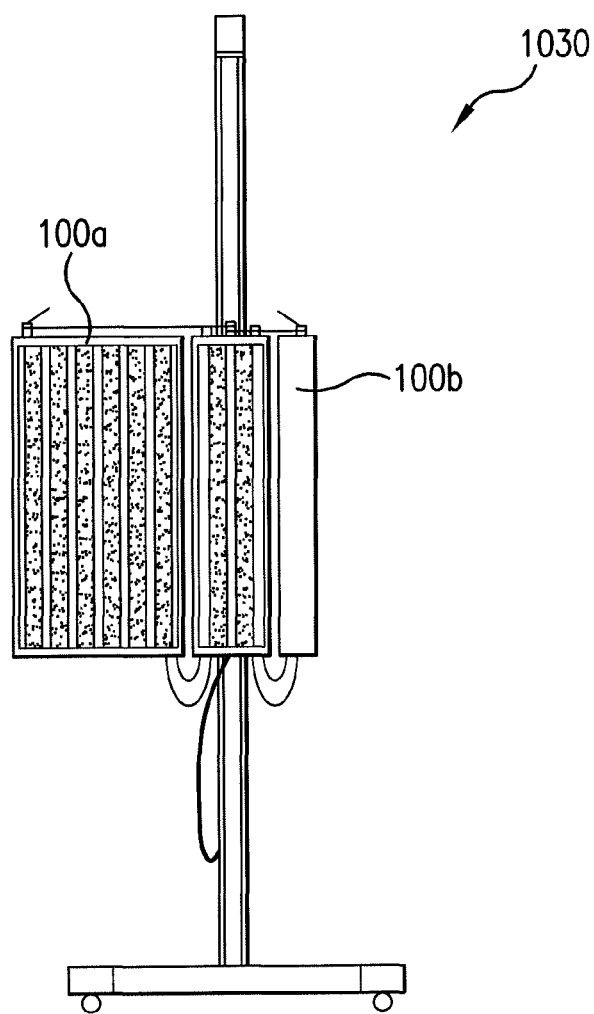
FIG. 8 is a front view of one embodiment of the disclosed subject matter in the right-forward position.
Figure 9:
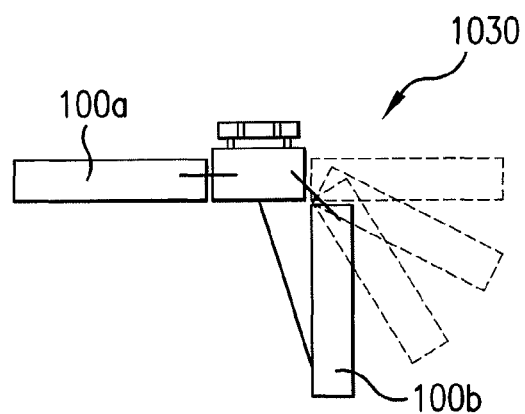
FIG. 9 is a top view of the embodiment depicted in FIG. 8.

FIGS. 8 and 9 illustrate the device configured in the right-forward position 1030. The second panel 100b has been pulled forward while the first panel 100a remains in a flat position.

Figure 10:
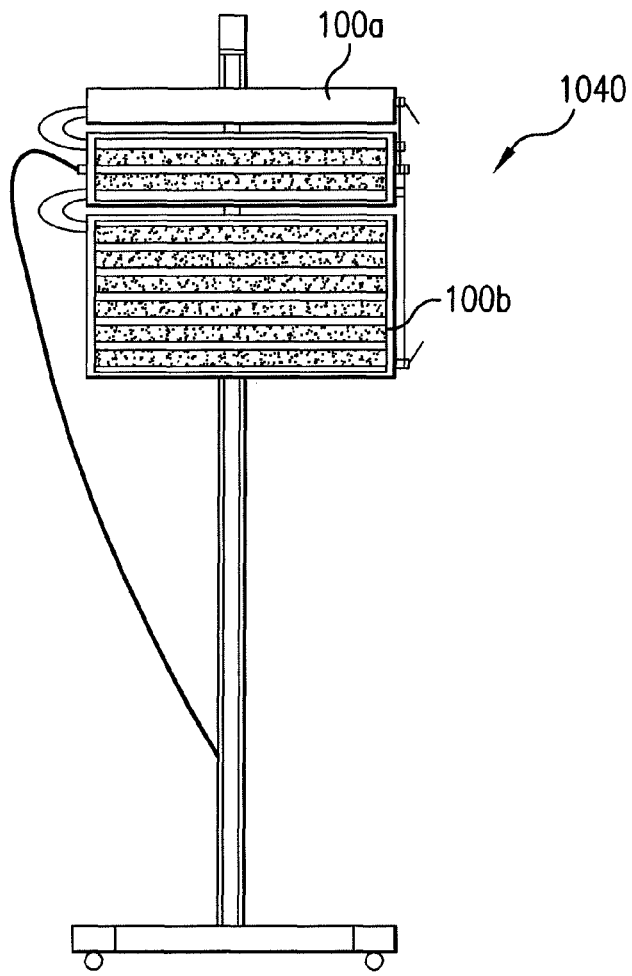
FIG. 10 is a front view of one embodiment of the disclosed subject matter in the high position.
Figure 11:
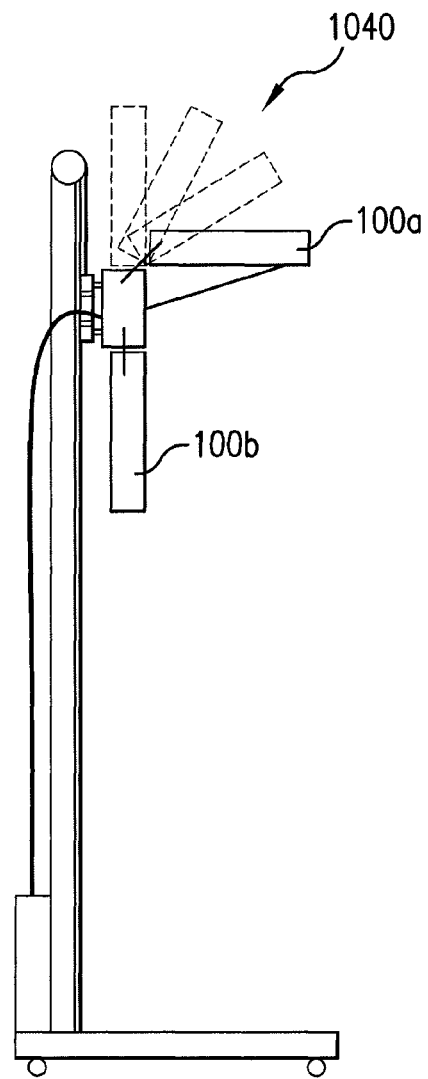
FIG. 11 is a side view of the embodiment depicted in FIG. 10.

FIGS. 10 and 11 illustrate the device configured in the high position 1040. The first panel 100a has been pulled forward while the second panel 100b remains in a flat position. The panels have been rotated to the 90-degree rotation position 1010 and raised to the top of the upright support 200.

Figure 12:
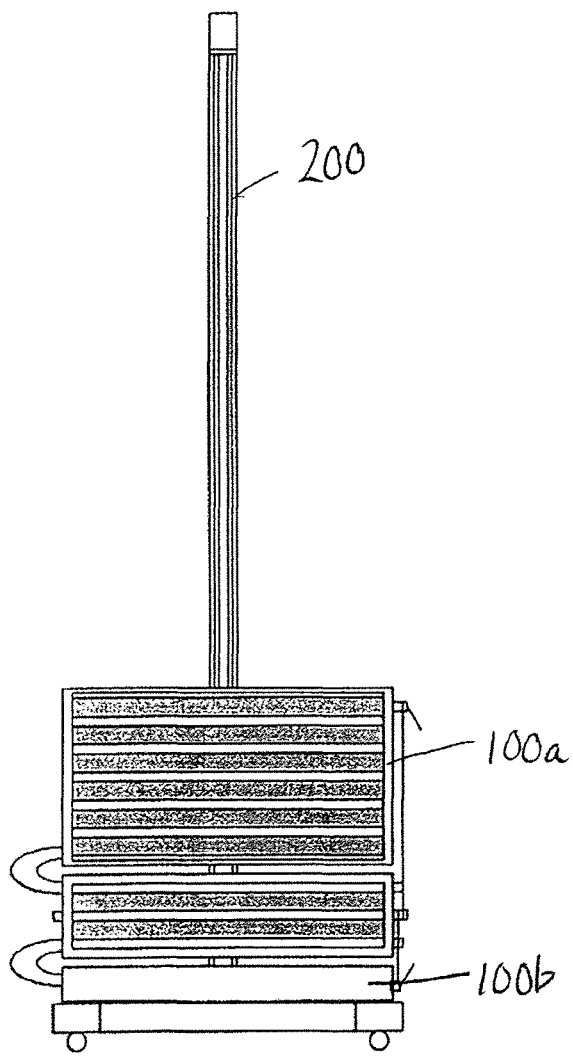
FIG. 12 is a front view of one embodiment of the disclosed subject matter in the low position.
Figure 13:
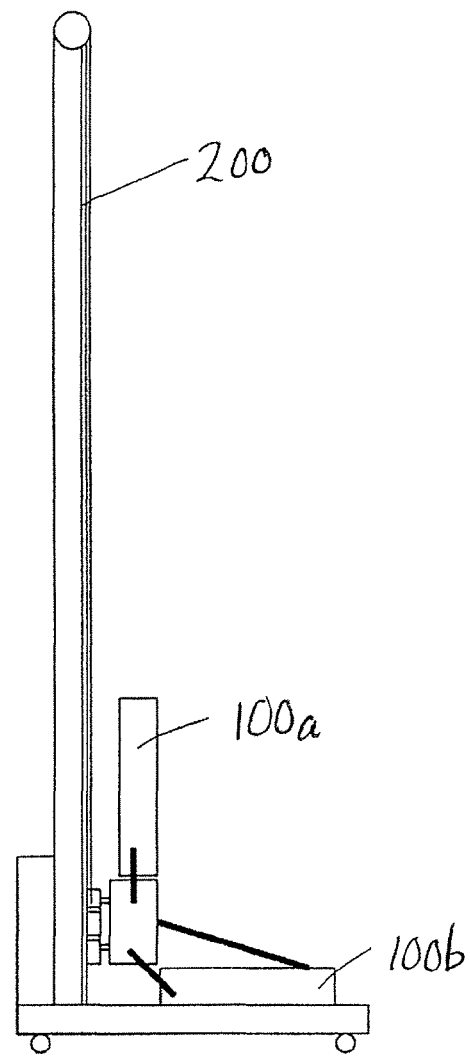
FIG. 13 is a side view of the embodiment depicted in FIG. 12.
Figure 14G:
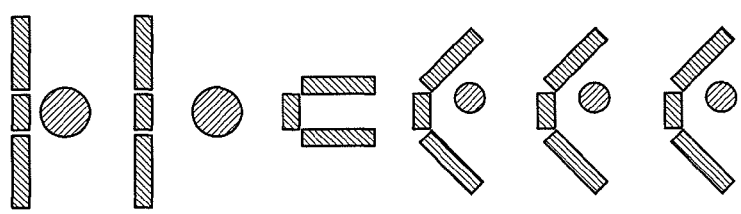
FIGS. 14(a)-(g) are illustrative diagrams showing how the device can be configured to treat various areas of the body.
Figure 14C:
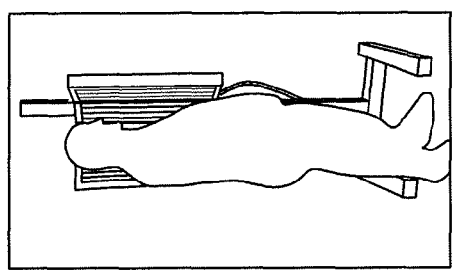
Figure 14F:
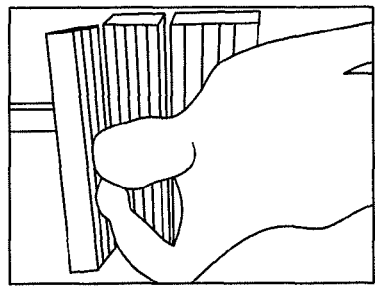
Figure 14B:
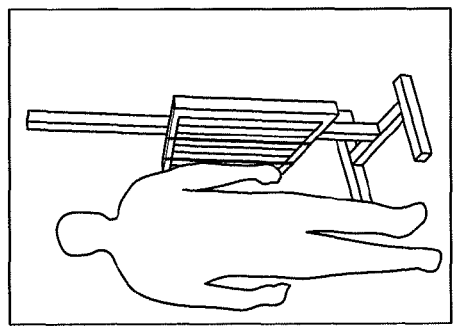
Figure 14E:
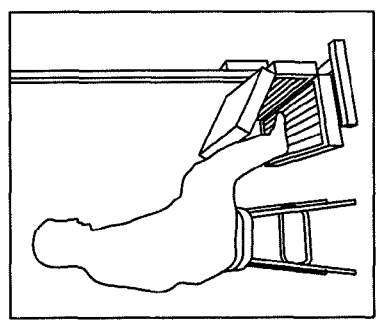
Figure 14A:
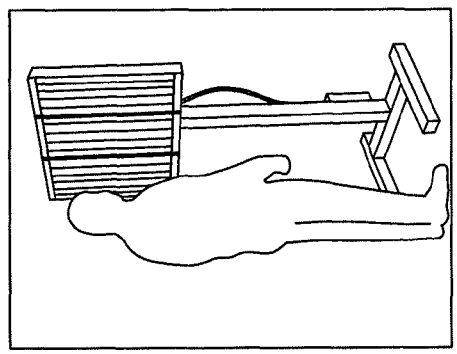
Figure 14D:
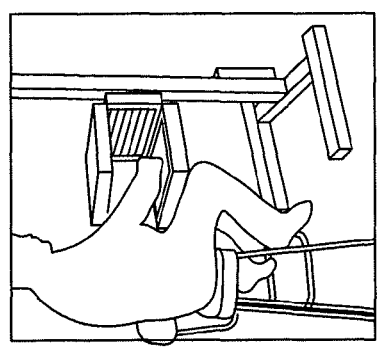

FIGS. 12 and 13 illustrate the device configured in the low position 1050. The second panel 100b has been pulled forward while the first panel 100a remains in a flat position. The panels have been rotated to the 90-degree rotation position 1010 and lowered to the bottom of the upright support 200.

As illustrated in FIGS. 14(a)-(g), the device 10 can be configured to provide various methods to treat various body parts. To treat the upper or lower body, for example, the panels 100 can be rotated into the starting position 1000, raised or lowered to the appropriate height, and either folded forward to surround the body or unfolded to lie in the same plane. To treat the hands, for example, the panels 100a and 100b can be folded forward to face each other, rotated to the 90-degree position 1010 so as to be parallel to the floor, and lowered to the appropriate height (perhaps table height). Various other configurations can also be used to conform to different parts of the body which need treatment.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

The invention claimed is:

1. A configurable phototherapy device for selectively providing ultraviolet therapy to the skin of one or more body parts of a user, comprising:
    a center panel comprising one or more ultraviolet sources;
    a first panel comprising one or more ultraviolet sources connected to the center panel;
    a second panel comprising one or more ultraviolet sources connected to the center panel;
    an upright support with a swivel plate disposed in a track on the upright support, the track extending along the entire length of the upright support, said center panel rotatably mounted on the swivel plate, to allow said center panel, said first panel and said second panel to be positioned in proximity to the head, the feet, or a position between the head and the feet of the user via vertical positioning of the swivel plate along the track and rotational positioning of the center panel about the swivel plate to selectively provide ultraviolet therapy to said skin of one or more body parts with ultraviolet light; and
    a base onto which said upright support is fixed.

2. The device of claim 1, further comprising a pulley system that allows said swivel plate to be moved vertically along said track on the upright support.

3. The device of claim 2, wherein said swivel plate is connected to a cable in said pulley system.

4. The device of claim 1, further comprising a first cam between said first panel and said swivel plate and a second cam between said second panel and said swivel plate, said first and second cams allowing said first and second panels to fold forward.

5. The device of claim 1, further comprising a spring running in substantially the same direction as said upright support, said spring being connected to said swivel plate and allowing said swivel plate to be moved up and down said upright support.

6. The device of claim 1, further comprising a gear system that allows said swivel plate to be moved up and down said upright support.

* * * * *